(12) United States Patent
Hebert et al.

(10) Patent No.: US 8,201,994 B2
(45) Date of Patent: Jun. 19, 2012

(54) FLEXIBLE THERMAL CYCLE TEST EQUIPMENT FOR CONCENTRATOR SOLAR CELLS

(75) Inventors: Peter H. Hebert, Glendale, CA (US); Randolph J. Brandt, Palmdale, CA (US)

(73) Assignee: The Boeing Company, Chicago, IL (US)

( * ) Notice: Subject to any disclaimer, the term of this patent is extended or adjusted under 35 U.S.C. 154(b) by 794 days.

(21) Appl. No.: 12/258,321

(22) Filed: Oct. 24, 2008

(65) Prior Publication Data

US 2010/0046575 A1    Feb. 25, 2010

Related U.S. Application Data

(60) Provisional application No. 61/091,284, filed on Aug. 22, 2008.

(51) Int. Cl.
*G01N 3/60*    (2006.01)
*G01N 27/416*    (2006.01)
(52) U.S. Cl. ........ 374/57; 250/372; 250/341.6; 324/431
(58) Field of Classification Search ............ 374/57, 374/32, 33, 39, 141, 121, 163, 183; 136/290; 320/101; 250/372, 341.6; 324/426, 430, 431, 433
See application file for complete search history.

(56) References Cited

U.S. PATENT DOCUMENTS

| | | | | |
|---|---|---|---|---|
| 4,129,823 | A * | 12/1978 | van der Pool et al. | ... 324/761.01 |
| 4,924,096 | A * | 5/1990 | Mroczkowski et al. | ... 250/341.2 |
| 5,894,341 | A * | 4/1999 | Nishi et al. | ........................ 355/68 |
| 5,949,212 | A * | 9/1999 | Cherry | ........................... 320/101 |
| 7,359,063 | B2 | 4/2008 | Jungwirth | |
| 7,868,631 | B2 * | 1/2011 | Chen | ........................ 324/754.23 |
| 2008/0223441 | A1 | 9/2008 | Jungwirth | |

OTHER PUBLICATIONS

IEC 62108, International Standard, Concentrator photovoltaic (CPV) modules and assemblies—Design qualification and type approval, Dec. 2007, Edition 1.0, International Electrotechnical Commission, Geneva, Switzerland.

* cited by examiner

*Primary Examiner* — Amy Cohen Johnson
(74) *Attorney, Agent, or Firm* — Clifford Cousins

(57) ABSTRACT

A system and method for performing thermal stress testing of photovoltaic solar cells is presented. The system and method allows rapid testing of photovoltaic solar cells under controllable thermal conditions. The system and method presents a means of rapidly applying thermal stresses to one or more photovoltaic solar cells in a consistent and repeatable manner.

39 Claims, 3 Drawing Sheets

FLEXIBLE THERMAL CYCLE TEST EQUIPMENT FOR CONCENTRATOR SOLAR CELLS

CROSS REFERENCE TO RELATED APPLICATIONS

This application claims the benefit of U.S. Application No. 61/091,284, filed Aug. 22, 2008.

U.S. GOVERNMENT RIGHTS

This invention was made with Government support under DE-FC36-07G017052 awarded by the Department of Energy. The Government has certain rights in this invention.

FIELD

Embodiments of the subject matter described herein relate generally to a system and method for performing thermal stress testing of photovoltaic solar cells.

BACKGROUND

Solar cells, for example photovoltaic cells (PVCs), have been used for many years to generate electrical energy from sunlight. Hereafter, solar cells and PVCs will be used interchangeably and refer to cells that generate electrical power from exposure to light. Solar panels, which typically include many individual cells, have been deployed in space and terrestrial applications.

Terrestrial photovoltaic cells may be exposed to "multiple" sun sources using mirrors, reflectors, and/or lenses that concentrate sunlight into a smaller area, which results in higher radiation energy per square unit of area. Such concentration is desirable to generate higher current per cell. This concentrated level of energy generates high levels of heat that places stresses on the internal structures of the PVC as well as electrical connections and mechanical attachment points. Temperature gradients often develop between adjacent portions of the PVC.

Over time, these elevated temperatures and temperature gradients degrade the performance of PVCs and can trigger failures in the PVC, electrical connections or mechanical attachment points. Understanding the conditions under which PVCs fail enables engineers to develop solutions to mediate design problems within the PVCs and associated structures. Stress testing can assist engineering in developing failure rate metrics useful for system integrators that use PVCs in commercial applications.

Accordingly, test equipment and technologies for terrestrial photovoltaic cells are designed to test PVCs not only by approximating the incident light and environmental conditions likely to be seen by the PVCs, but also by thermally stressing the PVCs to determine the long term effects of thermal stresses on the PVCs. These methods can involve creating higher thermal stresses and sharper temperature gradients than typically would be seen in commercial applications. Creating these thermal stresses allow characterization of the PVCs in comparatively shorter periods of time.

Recreating the thermal stresses on the PVC can be accomplished in various ways. Current tests include exposing the PVCs to concentrated sunlight for extended periods of time, placing PVCs in thermal cycling chambers to simulate different thermal conditions, and applying electrical currents to stress the PVCs and electrical connections.

Testing using natural light is not always possible or practical. Natural light is only present for a portion of each day and is affected by weather such as clouds. Additionally, seasonal differences in some latitudes can greatly affect the number of available testing hours in a day. Further, the sun's angle changes throughout the day, requiring not only that the sun be tracked accurately for any test, but also that the test account for the altered solar output as the sun is filtered through different amounts of atmosphere throughout the day.

Unlike photovoltaic cells designed for outer space applications, terrestrial photovoltaic cells can be exposed to sunlight that is "filtered" through different atmospheric and/or environmental conditions. Moreover, the altitude at which the cells will be deployed can influence the spectral (wavelength) characteristics of sunlight. For example, the spectral characteristics of sunlight that reaches cells located in Sao Paolo, Brazil are different than the spectral characteristics of sunlight that reaches cells located in Phoenix, Arizona. Consequently, testing using natural light in one location may not be entirely predictive of the PVC's response in another location.

Many thermal tests take comparatively long periods of time to perform. Thermal test methods include placing the PVC to be tested in a controlled temperature environment, such as a thermal cycle chamber where inside the chamber the ambient temperature can be controlled. The ambient temperature is then cycled to different temperatures for varying periods of time, and then the performance of the PVC is measured to determine how the PVC was affected. Generally it takes some time for all the components to equalize with the internal ambient temperature using a thermal cycle chamber, and therefore cycle times for some tests can be fairly long, lasting from minutes to hours for each cycle.

Moreover, thermal cycle chambers typically are not representative of operating conditions in the field. Thermal cycle chambers convectively heat or cool the PVCs test samples evenly over a relatively long period of time. In contrast, the field temperature stresses typically occur much faster. Also the distribution of heat in the field will generally tend to be non-uniform across the entire PVC assembly. For example, in a thermal cycle chamber, the temperature typically is consistent from the front to the rear of the solar cell and at the mechanical and electrical interconnections. In the field, however, sunlight heats the front of the PVC whereas the rear of the PVC is typically attached to a heat sink structure, creating a temperature gradient from the front of the PVC to the rear of the PVC. Also, in the field, the mechanical and electrical connections often receive relatively little or no heating from sunlight, but considerable heating from convection, heat conduction, or electrical current passing through them.

Another thermal test method is the dark forward thermal cycle. Often performed in a thermal cycle chamber, the dark forward thermal cycle involves forward biasing the PVC to generate current through the PVC. The generated current simulates approximately the amount of current that would be produced by illuminating the PVC with sunlight. Using the dark forward thermal cycle method, it is also possible to force more current through the PVC than would be possible using illumination alone.

Advantages over the prior art are herewith provided in the following disclosure.

SUMMARY

Presented is a system and method for performing thermal stress tests on Photovoltaic Cells (PVCs). In various embodiments, the system and method includes or utilizes a solar simulator for testing PVCs that configured to provide light that emulates the solar energy equivalent to between 500-5000 individual suns. This high level of solar energy helps to accurately characterize the performance of the cells in the intended application. The solar simulator may be configured to provide accurate spectral adjustability to simulate different types of sunlight conditions. In various embodiments, the system and method includes a thermal simulator for testing PVCs that is configured to thermally test a PVC with shorter cycle times and more accurately simulate the thermal stresses and thermal gradients that will be seen in the field.

Various embodiments of the system and method includes a thermal control system for rapidly heating and cooling solar cells. In one embodiment of the system and method the thermal control system manages the temperature of the PVCs during exposure to high concentration light as part of an illuminated thermal stress test. This illuminated thermal testing not only applies thermal stresses and temperature gradients in a similar manner to what would be seen in the field, but also generates current in the internal structures of the PVC in the same direction and similar manner to what would occur in actual operating conditions. Rapid heating and cooling of the PVCs permits shorter cycle times for accurately characterizing the long term performance of the PVC in less time.

The present system and method allows a repeatable and consistent level of thermal stress to be applied to each PVC. The features, functions, and advantages discussed can be achieved independently in various embodiments of the present invention or may be combined in yet other embodiments further details of which can be see with reference to the following description and drawings.

BRIEF DESCRIPTION OF THE DRAWINGS

The accompanying figures depict various embodiments of the flexible thermal cycle test equipment for concentrator solar cells. A brief description of each figure is provided below. Elements with the same reference number in each figure indicated identical or functionally similar elements. Additionally, the left-most digit(s) of a reference number indicate the drawing in which the reference number first appears.

DETAILED DESCRIPTION

Figure 1:
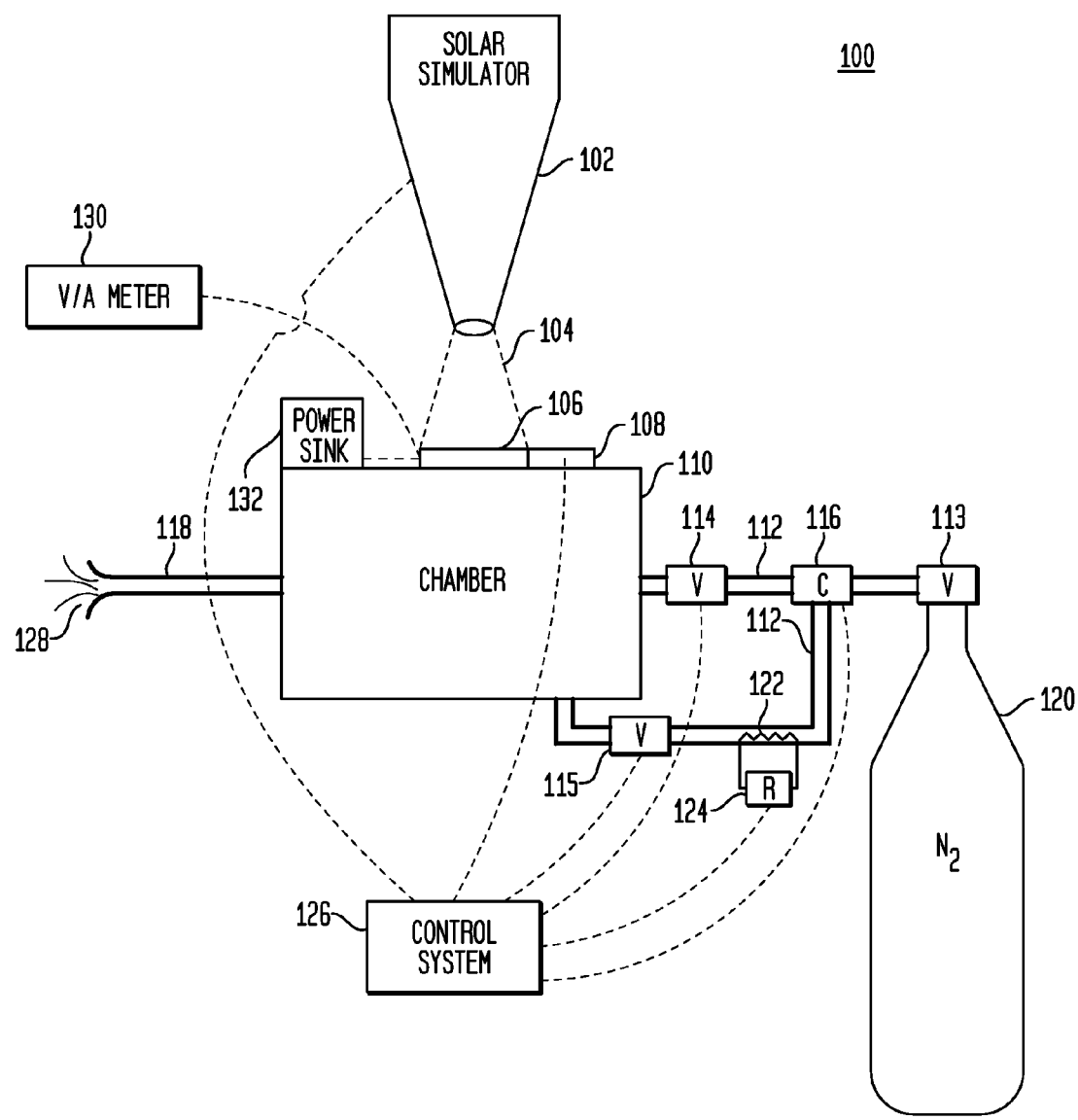
FIG. 1 is a schematic illustration of one embodiment of the flexible thermal cycle test equipment for concentrator solar cells.

The following detailed description is merely illustrative in nature and is not intended to limit the embodiments of the invention or the application and uses of such embodiments. Furthermore, there is no intention to be bound by any expressed or implied theory presented in the preceding technical field, background, brief summary or the following detailed description.

For the sake of brevity, conventional techniques related to photovoltaic cell design and testing, optics, optical filters, mirror design and manufacturing, and other functional aspects of the system (and the individual operating components of the system) may not be described in detail herein.

The following description refers to elements or nodes or features being "connected" or "coupled" together. As used herein, unless expressly stated otherwise, "connected" means that one element, node, or feature is directly joined to (or directly communicates with) another element, node, or feature, and not necessarily mechanically. Likewise, unless expressly stated otherwise, "coupled" means that one element, node, or feature is directly or indirectly joined to (or directly or indirectly communicates with) another element/node/feature, and not necessarily mechanically. Similarly, unless expressly stated otherwise, "in communication" means that one element, node, or feature is directly or indirectly joined to (or directly or indirectly communicates with) another element/node/feature, and not necessarily mechanically. Thus, although the figures depict one possible arrangement of elements, additional intervening elements, devices, features, or components may be present in an embodiment of the depicted subject matter.

This disclosure includes both a system and method for performing a wide variety of reliability tests for terrestrial concentrator solar cells, and the experimental methods that are enabled by the system and method. The various embodiments enable performing reliability tests in a manner that is both faster and more like operating conditions than many existing equipment and methods.

This disclosure addresses the problem of how to evaluate and improve reliability of terrestrial concentrator cells. This system and method discloses a means and method for stressing concentrator cells in a manner similar to operating conditions, and varying the magnitude of stresses in order to extrapolate from accelerated test conditions to normal operating conditions. The system and method further discloses a means and method for applying various stresses in various combinations to determine under which environments the solar cells require mitigation.

Equipment built and operated by test labs typically are dedicated pieces of equipment for performing various specific tests. Most existing thermal cycle equipment requires that parts under test are placed completely inside thermal cycle chambers.

Existing solutions require a larger capital investment for stand alone equipment for each test. Testing in thermal cycle chambers can be slow, and the thermal gradients placed on the parts are different then thermal gradients under operating conditions. A thermal cycle chamber generally is dedicated to a single temperature range and current biasing combination. Testing many conditions and combinations of conditions would require many thermal cycle chambers, or a significant amount of time as the tests would need to be performed sequentially in a single chamber.

Shown in FIG. 1 is a schematic view of one embodiment of the flexible thermal cycle test equipment for concentrator solar cells. A solar simulator 102 is a light source, or more generically, an electromagnetic radiation source, that directs an artificially generated beam of concentrated illumination 104 at a photovoltaic cell 106. The solar simulator 102 illuminates the photovoltaic cell 106 with concentrated illumination 104 matched to American Society for Testing Materials (ASTM) Air Mass 1.5 D (hereinafter AM1.5D) spectra in the intensity range 40 to 120 W/cmw (500 to 1300 suns). Standard reference spectra, including AM0, AM1.5, and AM2 are described in ASTM G-173-03 available from ASTM International, West Conshohocken, PA. The photovoltaic cell 106 is in communication with a temperature probe 108 and a chamber 110. The chamber 110 has an exhaust port 118 through which exhaust gasses 128 flow. Exhaust port 118 is in fluid communication with chamber 110. Valves 114 are in fluid communication with a coupler 116. Piping 112 connects valves 114 with chamber 110 and coupler 116. Inside of one piping 112 is a thermal resistor 122. Thermal resistor 122 is in electrical communication with temperature control system 126. Control system 126 is also in electrical communication with valves 114, temperature probe 108, and solar simulator 102. One or more electrical characteristic measuring devices 130, such as an analog or digital voltmeter, ammeter, etc., are in electrical communication with the photovoltaic 106 and collect voltage, amperage and power generation characteristics of the photovoltaic 106.

Previous high accuracy indoor testing generally was performed by flashing the lamp to avoid overheating issues in either the lamp or the solar cell. Obtaining a steady state light source necessary to perform accurate reliability testing generally meant going outdoors and using available natural light.

The solar simulator 102 in the embodiment of FIG. 1 is a steady state, high concentration light source. In various embodiments, the solar simulator 102 has a light intensity that is adjustable from approximately 400 to 1,000 suns and spectral filtering is adjustable to match different spectra (AMO, AM1.5, AM2, etc). In this context, it is understood that AMO refers to Air Mass zero radiation, also denoted as Air Mass Outer. AM1.5 refers to standard test conditions, while AM2 refers to the solar spectrum at earth's surface for average weather conditions with the spectrum that results when an AMO spectrum is attenuated by two path traversals through the atmosphere.

A homogenizer (not shown) in the solar simulator 102 provides uniform light intensity across a very well defined area with very little light fall off. This results in a beam of concentrated illumination 104 that illuminates the photovoltaic cell 106 evenly. In another embodiment, there are built-in diagnostics in the solar simulator 102 to verify spectral content and light intensity during testing. Performing a thermal test using the solar simulator 102 is more accurate than outdoor testing because the electromagnetic radiation from the solar simulator 102 is not subject to atmospheric conditions such as weather, the changing angle of the sun, or changes in atmospheric density. It also results in the ability to run more tests than outside because testing can be performed 24 hours per day. In an alternate embodiment, the beam of concentrated illumination 104 is non-uniform in intensity. In this embodiment, a photovoltaic cell 106 can be stress tested under light intensity gradations likely to occur in the field due to clouds or other solar obstructions. In one non-limiting example, the intensity of light varies by a factor of two from one portion of the photovoltaic cell 106 to another portion of the photovoltaic cell 106.

Figure 2:
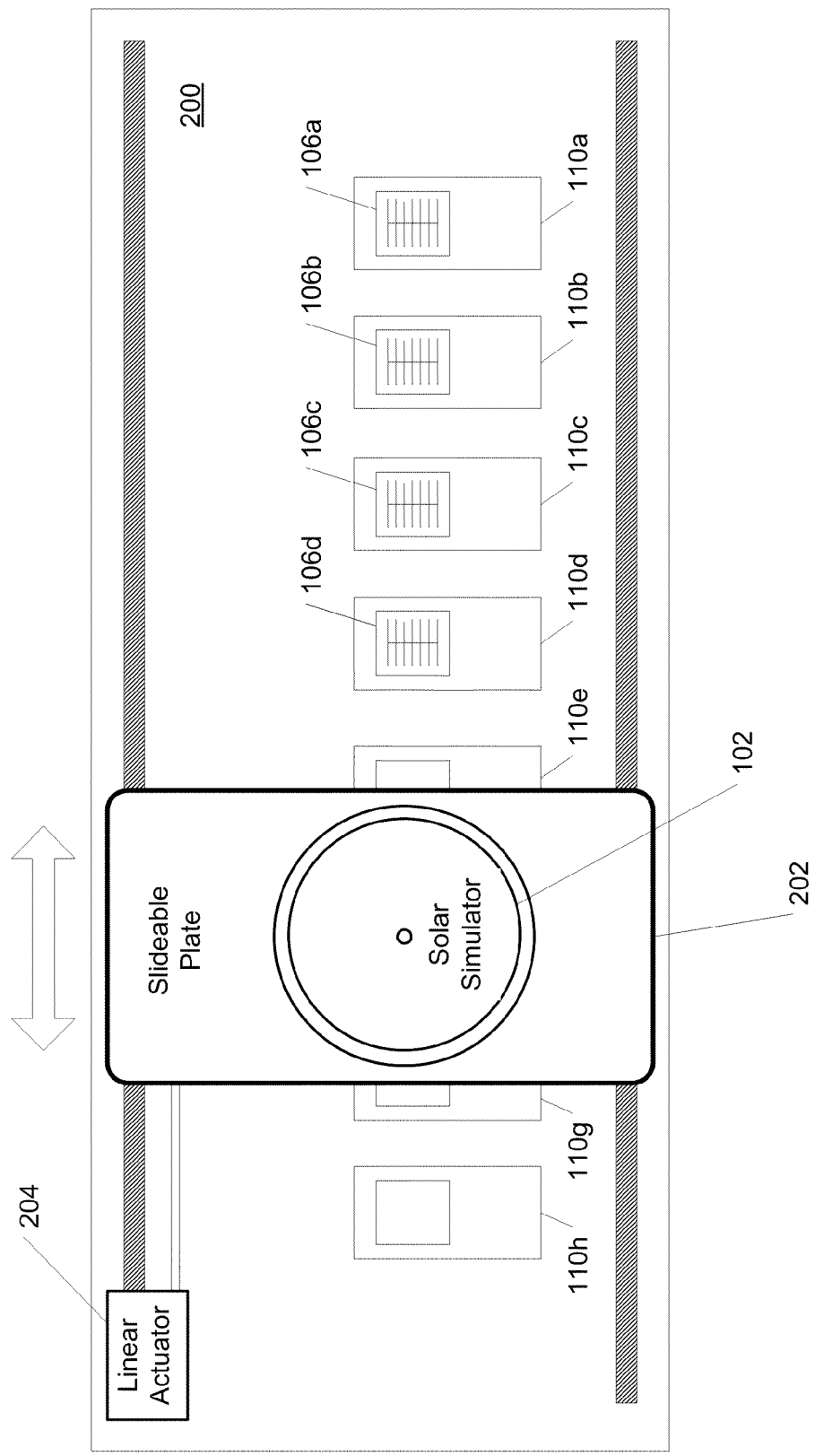
FIG. 2 is a schematic illustration of one embodiment of the flexible thermal cycle test equipment for concentrator solar cells with a slideable plate.

In another embodiment, illustrated in the multiple PVC test system 200 of FIG. 2, movement of the solar simulator 102 relative to the photovoltaic cells 106a, 106b, 106c, 106d (collectively 106) allows testing of multiple photovoltaic cells 106. This embodiment makes efficient use of the solar simulator 102. Moving the solar simulator 102 relative to the photovoltaic cells 106 allows testing multiple photovoltaic cells 106 with a single solar simulator 102. As shown in FIG. 2, multiple chambers 110a, 110b, 110c, 110d, 110e, 110f, 110g, and 110h (collectively 110), are connected to a carriage or slideable plate 202 that translates the solar simulator from chamber 110 to chamber 110.

The photovoltaic cells 106 are illustrated in a 1×8 matrix; but in other embodiments the photovoltaic cells 106 are mounted in other single or multi-dimensional arrangements, for example utilizing eight photovoltaic cells 106. For example, the photovoltaic cells 106 are mounted in a single column and the slideable plate 202 moved by a linear actuator 204. The slideable plate 202 can similarly be any positioning means as would be understood in the art. In other embodiments, the photovoltaic cells 106 are arranged in a circle on a rotary test plate and rotated under the solar simulator 102. In another embodiment, the solar simulator 102 is mounted on an x-y moveable gantry and moved above the particular photovoltaic cell 106 to be tested. In yet another embodiment, the solar simulator 102 is mounted in a gimbal and pointed at the photovoltaic cell 106 to be tested. In yet another embodiment, the beam of concentrated illumination 104 is moved by a mirror or optics, for example a first surface mirror.

Figure 3:
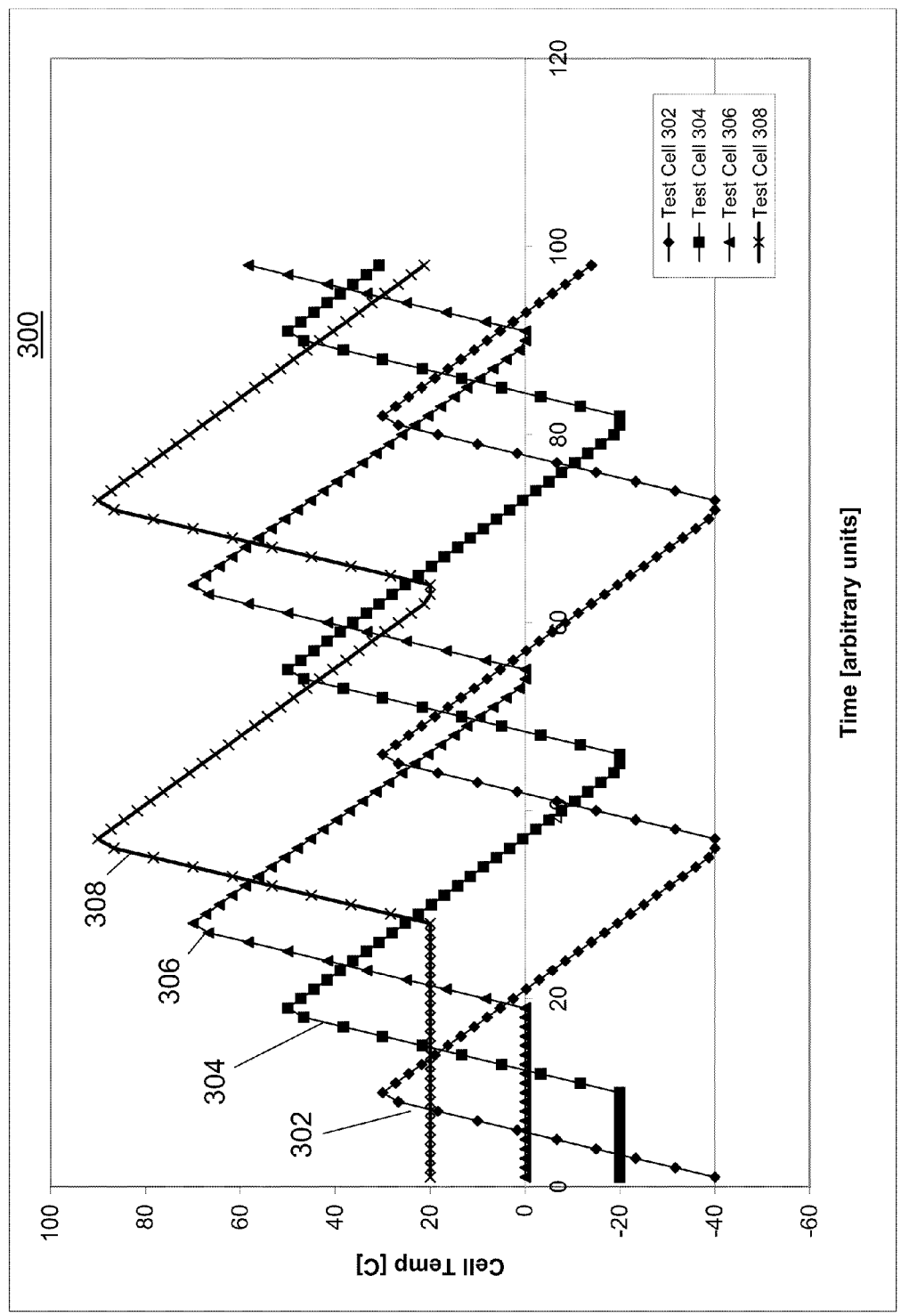
FIG. 3 is a graph of one embodiment of a thermal test of multiple photovoltaics using the flexible thermal cycle test equipment for concentrator solar cells.

Referring now to FIG. 3, a non-limiting example of batch testing of four photovoltaic cells 106 under a variety of test conditions is illustrated using a single solar simulator (not shown). Each test cell, 302, 304, 306, and 308 is cycled through a 70 degree temperature differential. Test cell 302 is first heated from −40 degrees Celsius and 30 degrees Celsius by illumination from the solar simulator, after which the solar simulator is moved to test cell 304 and test cell 302 is slowly cooled back to −40 degrees Celsius. Once the solar simulator is moved to test cell 304, test cell 304 is heated from −20 degrees Celsius and 50 degrees Celsius by illumination from the solar simulator, after which the solar simulator is moved to test cell 306. Similarly, test cells 306 and 308 are cycled between 0 degrees Celsius and 70 degrees Celsius and 20 degrees Celsius and 90 degrees Celsius respectively. This batch testing allows multiple photovoltaic cells 106 to be tested under a variety of test conditions using a single solar simulator.

The system includes a means for heating and cooling the photovoltaic cell 106 uniformly and rapidly. In one embodiment a thermal control system uses LN2 (liquid nitrogen gas) for cooling and heated GN2 (gaseous nitrogen gas) for heating. Returning to FIG. 1, a cylinder of liquefied nitrogen gas 120 has a safety valve 113 for easy replacement of the cylinder. When the safety valve 113 is open, nitrogen gas flows to the coupler 116 that directs nitrogen gas to two short lengths of piping 112, not illustrated to scale. One length of piping 112 connects to a cold gas valve 114 that leads directly into the heat exchanger, showing in this embodiment as a chamber 110. The system 100 is most efficient if this section of piping 112 is as short as possible, because as the liquefied nitrogen gas expands it absorbs heat and any expansion in the piping 112 is lost to the system 100. Another length of piping 112 connects to a hot gas valve 115 that also leads into the chamber 110. In this length of piping 112 is a thermal resistor 122, for example a 750 Watt heating element, connected to an electrical regulator 124. However, in other embodiment, any kind of heating element or means to heat the gas could be utilized to perform a similar function, for example a solid state heating element.

The photovoltaic cell 106 is in thermal communication with the chamber 110 such that cooling or heating the chamber 110 cools or heats the photovoltaic 106. In this embodiment, the photovoltaic cell 106 is secured to the top of the chamber 110 but is otherwise exposed to air and the ambient temperature of the test environment. The chamber 110 allows for rapid heat transfer and simulates the heat sink configuration of many field installations. Illuminating the front surface of the photovoltaic 106 with the solar simulator 102, and removing heat from the back surface of the photovoltaic 106 develops a thermal gradient across the photovoltaic 106 that is characteristic of actual field conditions. This creation of a thermal gradient across the photovoltaic 106 makes it possible to test the photovoltaic 106 under a realistic set of conditions likely to occur in the field. Other thermal cycling systems place test parts into uniform thermal environments that do not match thermal gradients or approximate operational thermal stresses. Thermal gradients across a photovoltaic test sample placed inside a thermal cycle chamber are not representative of operating conditions. In complex assemblies with different materials, the thermal gradients are important in generating appropriate stresses. This system 100 performs illuminated thermal cycling with very fast thermal responses, allowing the system to operate faster (reducing development time) or to operate more accurately with fewer temperature spikes when creating representative thermal stresses.

Illuminating the photovoltaic 106 with the solar simulator 102 also has advantages over other thermal cycle test methods. For example, the dark forward thermal cycle test method involves forward biasing the photovoltaic 106 to force current to flow through the photovoltaic 106 without requiring illumination of the photovoltaic 106. However, the dark forward thermal cycle test method does not produce identical internal stresses in the photovoltaic 106 as illumination of the photovoltaic 106. During the dark forward thermal cycle, current flows in the opposite direction through the photovoltaic 106 than the current direction from an illuminated photovoltaic 106. At the semiconductor level, forward biasing also uses a different internal mechanism than illumination. Illumination creates additional carriers for transferring current across the internal semiconductor structures of the photovoltaic 106. Forward biasing, instead of adding carriers, overcomes the internal voltage potential of the junction between P-doped and N-doped semiconductor regions (not shown), thereby making it easier for the existing carriers in the semiconductor to transfer current across the internal structures of the photovoltaic 106. Using illumination to generate current in the photovoltaic 106 with the solar simulator 102 advantageously stresses the internal structures of the photovoltaic 106 in a manner similar to operating conditions in the field.

To cool the photovoltaic 106, the control system 126 opens the cold gas valve 114, allowing gaseous nitrogen to flow from the cylinder of nitrogen 120 to the chamber 110. As the gas expands, the gas cools the chamber 110 and the photovoltaic cell 106. To heat the photovoltaic 106, the control system 126 opens the hot gas valve 115 allowing gaseous nitrogen to flow from the cylinder of nitrogen gas 120 through the piping 112 and across the thermal resistor 122. The electrical regulator 124 energizes the thermal resistor 122 which heats the nitrogen gas as it flows pasts the thermal resistor 122. In one embodiment, the thermal resistor 122 is energized at the same time the hot gas valve 115 is opened. In other embodiments, the thermal resistor 122 is energized just before or after the hot gas valve 115 is opened. In other embodiments, the photovoltaic cell 106 is in communication with a heating and cooling means (not shown) such as a compressed fluid heat exchange systems, such as a refrigeration device, or a solid state device such as a Peltier device.

Although the piping 112 is illustrated as two lengths of piping 112, in alternate embodiments a single length of piping 112 is utilized. Exhaust gasses 128 exit the system 100 through the exhaust pipe 126, which is vented to a safe location. Because nitrogen gas is utilized, it can normally be safely vented anywhere so long as the temperature of the exhaust gas 128 is not an issue.

In one embodiment the chamber 110 is made entirely or partially of aluminum, although any material having a high thermal conductivity that can withstand rapid temperature changes and pressure changes can be utilized. Pressures in the piping 112 and chamber 110 can reach 50 PSI or greater. The photovoltaic cells 106 are normally tested for the range of −40 C to 110 C, although temperatures for the gasses in the chamber 110 can be hotter or colder. The control system 126 thermally regulates the temperature between −60 degrees Celsius and 140 degrees Celsius. During periods where the control system 126 is allowing the temperature to change, it maintains the temperature to within plus or minus 3 degrees Celsius of the intended or desired temperature. Once the desired temperature is stabilized, or held constant, the control system 126 maintains the temperature to within plus or minus 1 degree Celsius. To regulate the temperature, the control system 126 measures the temperature of photovoltaic 106 using temperature sensor 108 and either opens the cold gas valve 114, or the hot gas valve 115 and energizes thermal resistor 122 accordingly. In this way, the system removes the heat added to the photovoltaic cell 106 by either the dark forward current or the concentrated illumination 104 from the solar simulator 102. In one embodiment, the temperature sensor 108 is a contact variety made of stainless steel; in another embodiment the temperature sensor 108 is a non-contact sensor (not shown) that measures temperature from a distance, for example an infrared (IR) sensor. The heating and cooling portions of the system 100, and in particular the chamber 110, are low mass and very close to the photovoltaic 106, so the temperature response is very fast.

In other embodiments, the solar simulator 102 applies high intensity ultraviolet (UV) exposure testing, for example approximately 2000 suns, while the system 100 regulates the temperature of the photovoltaic 106 at a desired temperature, for example 25 degrees Celsius. A means to measure instantaneous or cumulative exposure at wavelengths under 400 nm is also contemplated in this mode. In other embodiments, instead of the solar simulator 102, a current source (not shown) applies a forward bias to the photovoltaic 106 to create thermal stresses. In still other embodiments, there is no solar simulator 102 and the system 100 directly applies the thermal stresses to the photovoltaic 106. In still other embodiments, the solar simulator 102 is replaced by natural sunlight or concentrated natural sunlight.

One or more electrical measuring devices 130 collect voltage, amperage, power, and other electrical generation characteristics, or output characteristics, of the photovoltaic 106. In various embodiments, collection of these electrical characteristics is performed during before thermal testing, during thermal testing, during portions of the thermal testing, after each individual thermal test cycles, and after thermal testing is completed. In one embodiment, when illuminated, the photovoltaic 106 produces currents of between approximately 0.1 amps and 18 amps at 5 volts. In this embodiment, the measuring device 130 sinks the electrical current generated by the photovoltaic 106. In this embodiment, the measuring device 130 functions as a power sink 132 for dissipating the energy produced by the photovoltaic 106 during solar testing. In embodiments, a separate power sink 132, for example a passive resistor or resistor network, dissipates the current produced by the photovoltaic 106. In still further embodiments, a power sink 132 is in communication with a chamber 110 and cooled.

The system simulates thermal life-cycles for solar cells and is therefore applicable for performing thermal stress testing of photovoltaic cells 106. Stress testing is performed to project the useful life of the photovoltaic cell 106. Stress testing also assists PVC designers in determining the root cause of early failures.

The system and method is also applicable to performing burn-in or heat soaking. Electronic component failure typically follows a well known "bathtub curve" failure rate curve. Statistically there are often a significant number of early component failures, sometimes referred to as infant mortality. This is followed by a typical longer span of time whereby there is a statistically decreasing or stable component failure rate, ending typically when the component failure rate begins to increase again. This span of time generally defines the useful life of the component. Burn-in or heat soaking helps to remove components that would otherwise fail in the field, enabling the majority of components placed into operation to be in their comparatively long "useful life" portion of their life cycle.

Burn-in or heat soaking is often performed at elevated temperatures and elevated voltages. It is therefore important to stress the photovoltaic cell 106 enough to eliminate those components that would statistically fail prematurely, while not stressing the photovoltaic cell 106 in such a way that it reduces the useful life of the photovoltaic cell 106, adversely decreases the factory yield of photovoltaic cells 106, or introduces a higher failure photovoltaic cell 106 failure rate in the field. The system 100 regulates the thermal characteristics of the photovoltaic cell 106 ensuring that the photovoltaic cell 106 is not overstressed.

In the embodiment illustrated in the multiple PVC test system 200 of FIG. 2, movement of the solar simulator 102 relative to the photovoltaic cells 106 allows for testing multiple photovoltaic cells 106 with a single solar simulator 102. One thermal stress test is to cool a photovoltaic cell 106 to −40 degrees Celsius, then bringing the temperature of the photovoltaic cell 106 to 25 degrees Celsius, and finally applying concentrated illumination 104 and maintaining the temperature of the photovoltaic cell 106 at 110 degrees Celsius for a period of time. Because the solar simulator 102 is illuminating each photovoltaic cell 106 for a portion of the entire cycle, the solar simulator 102 can illuminate one photovoltaic cells 106 for one part of the cycle, while another photovoltaic cell 106 is being cooled −40 degrees Celsius, and another photovoltaic cell 106 is being heating to 25 degrees Celsius. In this embodiment, up to eight photovoltaic cells 106 are tested using a single solar simulator 102.

In other thermal test embodiments, the thermal control system generates the thermal stresses, either alone or in conjunction with dark forward current, and the solar simulator 102 is utilized for generating current in photovoltaic cell 106 for testing the electrical output characteristics of the photovoltaic cell 106. In these embodiments, additional photovoltaic cells 106 can be tested using a single solar simulator 102.

Conclusion

The embodiments of the invention shown in the drawings and described above are exemplary of numerous embodiments that may be made within the scope of the appended claims. It is contemplated that numerous other configurations of a flexible thermal cycle test equipment for concentrator solar cells may be created taking advantage of the disclosed approach. It is the applicant's intention that the scope of the patent issuing herefrom will be limited only by the scope of the appended claims.

What is claimed is:

1. An illuminated thermal test system, comprising:
   a power sink operably adapted to sink an electrical current from a photovoltaic cell;
   an electromagnetic radiation source directing an electromagnetic radiation at said photovoltaic cell such that said electromagnetic radiation constitutes a principle source of electrical current in said photovoltaic cell;
   a temperature sensor for detecting a temperature of said photovoltaic cell;
   a temperature control means operably adapted to modify said temperature of said photovoltaic cell, wherein said temperature control means comprises a chamber in communication with said photovoltaic cell and comprises a means for controlling a flow of a fluid into said chamber; and
   a measuring means for measuring said electrical current from said photovoltaic cell, wherein said power sink is in communication with said chamber and said power sink is cooled by said flow of said fluid into said chamber.

2. The system of claim 1, further comprising a photovoltaic cell operably adapted to provide an electrical current when exposed to electromagnetic radiation.

3. The system of claim 1, wherein said fluid is a gas selected from the group consisting of an ambient temperature nitrogen gas, a heated nitrogen gas, and a liquefied nitrogen gas.

4. The system of claim 1, wherein said temperature control means is adapted to control said temperature between −60 degrees Celsius and 140 degrees Celsius.

5. The system of claim 4, wherein said temperature control means is adapted to control said temperature within plus or minus 3 degrees Celsius of an intended temperature when said intended temperature is being changed and within plus or minus 1 degree Celsius of an intended temperature when said intended temperature is being held constant.

6. The system of claim 1, wherein said electromagnetic radiation is a concentrated electromagnetic radiation between 400 and 2000 suns.

7. The system of claim 1, wherein said electromagnetic radiation incident upon said photovoltaic cell is substantially uniform.

8. The system of claim 1, wherein said electromagnetic radiation has a spectral content selected from the group consisting of UV, AM0, AM1.5, AM1.5D, and AM2.

9. The system of claim 1, wherein said electromagnetic radiation is UV, said electromagnetic radiation is approximately 2000 suns, and said temperature is held constant at 25 degrees Celsius.

10. The system of claim 1, where said electromagnetic radiation is AM1.5D, and said electromagnetic radiation is between 400 and 1300 suns.

11. The system of claim 1, wherein said electrical current is between approximately 0.1 amp and 18 amps when said electromagnetic radiation is incident upon said photovoltaic cell.

12. The system of claim 1, further comprising:
   a plurality of photovoltaic cells,
   and wherein said electromagnetic radiation source is directed at a first photovoltaic cell of said plurality of photovoltaic cells, while concurrently said temperature of each of said remainder of said plurality of photovoltaic cells is modified by said temperature control means.

13. The system of claim 12, further comprising an orienting system adapted to selectively orient said electromagnetic radiation source to direct said electromagnetic radiation towards at least one of said plurality of photovoltaic cells.

14. A system for performing illuminated thermal testing of a solar cell, comprising:
   an electromagnetic radiation source adapted to produce an output of illumination on a first portion of the solar cell;
   a heat exchanger in communication with a second portion of the solar cell, such that a temperature gradient exists between said first portion of the solar cell and said second portion of the solar cell;
   a temperature sensor for detecting a temperature of a solar cell portion; and
   a controller in communication with said temperature sensor, said controller regulating a flow of fluid into said heat exchanger to attain a desired temperature of a solar cell portion during the illuminated thermal testing of the solar cell, wherein an electrical current in the solar cell for the thermal testing of the solar cell is generated solely by applying said output of illumination to the solar cell.

15. The system of claim 14, wherein said electromagnetic radiation source produces an output of concentrated illumination between 400 and 2000 suns.

16. The system of claim 15, wherein a spectral content of said output of concentrated illumination is selected from the group consisting of UV, AM0, AM1.5, AM1.5D, and AM2.

17. The system of claim 15, wherein said output of concentrated illumination is substantially uniform.

18. The system of claim 14, wherein said spectral content of said output of concentrated illumination is UV, said output of concentrated illumination is approximately 2000 suns, and said temperature is held constant at 25 degrees Celsius.

19. The system of claim 14, where said spectral content of said output of concentrated illumination is AM1.5D, and said output of concentrated illumination is between 400 and 1300 suns.

20. The system of claim 14, further comprising a power sink operably adapted to sink an electrical current of between approximately 0.1 amp and 18 amps at approximately 5 volts when said output of illumination is incident on said first portion of said solar cell.

21. The system of claim 14, wherein said fluid is a gas selected from the group consisting of an ambient temperature nitrogen gas, a heated nitrogen gas, and a cold nitrogen gas.

22. The system of claim 14, wherein said temperature sensor is configured to detect a temperature of said heat exchanger.

23. The system of claim 14, wherein said temperature controller is adapted to control said desired temperature between −60 degrees Celsius and 140 degrees Celsius.

24. The system of claim 14, wherein said temperature controller is adapted to control said desired temperature to within plus or minus 3 degrees Celsius of a said desired temperature when said desired temperature is being changed and within plus or minus 1 degree Celsius of said desired temperature when said desired temperature is being held constant.

25. The system of claim 14, further comprising a sensor for measuring a characteristic of an electrical energy produced by the solar cell.

26. The system of claim 14, further comprising:
an orienting system adapted to selectively direct said output of illumination onto at least one of a plurality of solar cell test samples.

27. A method for rapid testing of a solar cell, comprising:
(a) cooling the solar cell to a first temperature by thermal conduction via a cooling fluid;
(b) heating the solar cell to a second temperature;
(c) maintaining said second temperature in the solar cell for a test period;
(d) repeating steps (a), (b), and (c); and
(e) measuring an electrical characteristic of the solar cell.

28. The method of claim 27, further comprising:
releasing said cooling fluid into a chamber in communication with the solar cell.

29. The method of claim 27, wherein said cooling fluid is a liquefied nitrogen gas, said liquefied nitrogen gas expanding in said chamber to effect said cooling.

30. The method of claim 27, wherein said heating comprises releasing a heating fluid into said chamber.

31. The method of claim 27, wherein said heating comprises applying a forward bias electrical potential across the solar cell.

32. The method of claim 27, wherein said heating comprises directing an electromagnetic radiation at the solar cell such that an electrical current is generated principally by the solar cell.

33. The method of claim 32, wherein said electrical current is between 0.1 amp and 18 amps.

34. The method of claim 32, wherein said electromagnetic radiation has an amplitude between 400 and 2000 suns; wherein said electromagnetic radiation has a spectral content selected from the group consisting of AM0, AM1.5, AM1.5D, and AM2; and wherein said electromagnetic radiation is selected from the group consisting of a substantially uniform output of electromagnetic radiation and a non-uniform output of electromagnetic radiation.

35. The method of claim 27, wherein a plurality of solar cells are simultaneously tested, and further comprising:
directing said electromagnetic radiation at each of said plurality of solar cells in succession while simultaneously cooling each of said plurality of solar cells to which said electromagnetic radiation is not directed.

36. The method of claim 27, wherein said first temperature is −40 degrees Celsius and said second temperature is selected from the group consisting of 25 degrees Celsius, and 110 degrees Celsius.

37. The method of claim 27, wherein said first temperature is selected from the group consisting of −40 degrees Celsius, −20 degrees Celsius, 0 degrees Celsius, and 20 degrees Celsius, and said second temperature is 70 degrees greater than said first temperature.

38. The method of claim 27, wherein said maintaining said second temperature in the solar cell comprises releasing a fluid into said chamber selected from the group consisting of said cooling fluid and said heating fluid.

39. A system for performing illuminated thermal testing of a solar cell, comprising:
an electromagnetic radiation source adapted to produce an output of illumination on a first portion of the solar cell;
a heat exchanger in communication with a second portion of the solar cell, such that a temperature gradient exists between said first portion of the solar cell and said second portion of the solar cell;
a temperature sensor for detecting a temperature of a solar cell portion, and
a controller in communication with said temperature sensor, said controller regulating a flow of fluid into said heat exchanger to attain a desired temperature of a solar cell portion during the illuminated thermal testing of the solar cell; and
a power sink operably adapted to sink an electrical current of between approximately 0.1 amp and 18 amps at approximately 5 volts when said output of illumination is incident on said first portion of said solar cell, wherein said power sink is in communication with said heat exchanger and said power sink is cooled by said heat exchanger.

* * * * *